United States Patent [19]

Weiss

[11] Patent Number: 5,705,666
[45] Date of Patent: Jan. 6, 1998

[54] PROCESS FOR THE PREPARATION OF CRYSTALLINE O-ISOPROPYLISOUREA HYDROCHLORIDE

[75] Inventor: Stefan Weiss, Trostberg, Germany

[73] Assignee: SKW Trostberg Aktiengesellschaft, Trostberg, Germany

[21] Appl. No.: 665,421

[22] Filed: Jun. 19, 1996

[30] Foreign Application Priority Data

Jun. 27, 1995 [DE] Germany ............ 195 23 205.4

[51] Int. Cl.⁶ .............................. C07C 275/70
[52] U.S. Cl. .............................. 558/8
[58] Field of Search .............................. 558/8

[56] References Cited

U.S. PATENT DOCUMENTS

| | | | |
|---|---|---|---|
| 2,039,514 | 5/1936 | Battegay | 558/8 |
| 3,551,489 | 12/1970 | Schaefer | 558/8 |
| 3,670,022 | 6/1972 | Schaefer | 558/8 |
| 3,931,316 | 1/1976 | Weiss | 558/8 |

FOREIGN PATENT DOCUMENTS

| | | |
|---|---|---|
| 1948370 | 4/1971 | Germany. |
| 2358904 | 6/1975 | Germany. |
| 2708973 | 9/1978 | Germany. |
| 1194313 | 6/1970 | United Kingdom. |

OTHER PUBLICATIONS

Canadian Journal of Research, 1 (1929), Studies in Iso–Ureas And Iso–Ureides, by S. Basterfield and E.C. Powell, pp. 261–271.

Database CAPLUS on STN, Columbus: Chemical Abstracts Service, Acc. No. 1971:124906, DE 1948370 (Prietzel), abstract, Apr. 1971.

*Primary Examiner*—Michael G. Ambrose
*Attorney, Agent, or Firm*—Felfe & Lynch

[57] ABSTRACT

Disclosed is a process for the preparation of crystalline O-isopropylisourea hydrochloride, wherein cyanamide, chloroformamidinium chloride and isopropanol are reacted, an aprotic solvent preferably selected from the group consisting of ketones, ethers, esters and acetals, is added to the reaction mixture before, during and/or after the reaction and, optionally after cooling the reaction solution, the crystalline reaction product is separated off. O-isopropylisourea hydrochloride is obtained in a very pure and coarse crystalline form by the process of the invention.

16 Claims, No Drawings

PROCESS FOR THE PREPARATION OF CRYSTALLINE O-ISOPROPYLISOUREA HYDROCHLORIDE

BACKGROUND OF THE INVENTION

The present invention is concerned with a process for the preparation of crystalline O-isopropylisourea hydrochloride with high purity which is an important intermediate for the preparation of plant protection agents and medicaments.

The preparation of this compound has been described many times but hitherto it has not been possible to obtain pure O-isopropylisourea hydrochloride in crystalline form. Thus, for example, Basterfield and Powell have described the reaction of cyanamide with hydrogen chloride in isopropanol (cf. Canad. J. Res., 1, 261/1929). The product is hereby obtained in the form of a yellow, viscous oil which cannot be crystallised out of an ethereal solution even at −10° C.

According to U.S. Pat. No. 3,551,489 and G. B. Pat. No. 1,194,313, O-isopropylisourea hydrochloride can be obtained in the form of a syrup by the reaction of cyanamide with concentrated hydrochloric acid and isopropanol from which O-isopropylisoures picrate can be isolated but not the hydrochloride itself in crystalline form.

Thus, according to the prior art, the preparation of crystslline and pure O-isopropylisourea hydrochloride by the reaction of cyanamide with isopropanol in the presence of hydrogen chloride or hydrochloric acid is not possible since, in the case of this reaction, there can only be obtained an impure compound in the form of an oil or syrup. Handling the picrate isolated therefrom is dangerous on a technical scale.

Furthermore, purification of the compound by recrystallisation is not possible and the use of impure compounds in the synthesis of valuable active materials, for example in the synthesis of pharmaceuticals, is often not possible or involves great problems.

A further disadvantage of the above-described processes is the fact that it is necessary to work with gaseous hydrogen chloride or with concentrated hydrochloric acid both of which strongly attack metallic work materials, for example stainless steel, end destroys them by corrosion.

Finally, in DE-OS 19 48 370 there is also described the preparation of O-isopropylisourea hydrochloride by heating chloroformamidinium chloride in isopropanol. After an extended refrigeration period, a solid product with s melting point of 57 to 61° C. which is, however, still contaminated with chloro-formamidinium chloride can be obtained.

On a technical scale, this process is also not suitable for the preparation of crystalline and pure O-isopropylisoures hydrochloride since a comparatively long standing at low temperatures is very laborious in the case of preparation on a technical scale.

Furthermore, in the case of the reaction of chloroformamidinium chloride with isopropanol, hydrogen chloride is liberated in equimolar amounts which respects only slowly and incompletely to give isopropyl chloride. Therefore, this reaction mixture also contains free hydrogen chloride, which is very corrosive.

In addition, the very readily volatile isopropyl chloride results as an undesired by-product. The separating off and destruction of this chlorohydrocarbon is very laborious and expensive since it cannot be permitted to escape into or otherwise enter the environment. Furthermore, as is known, isopropyl chloride belongs to the alkylation agents which possess mutagenic properties.

Finally, the O-isopropylisourea hydrochloride prepared in this way contains urea as an impurity since, as is known, in the case of heating, O-alky-lisourea hydrochlorides break down into urea and alkyl halides.

Therefore, it is the object of the present invention to provide a process for the preparation of O-isopropylisoures hydrochloride which does not have the the above-mentioned disadvantages of the prior art but rather, with a low technical expense and in an environmentally friendly manner, makes possible the preparation of a crystalline product with a high purity.

THE INVENTION

The present invention is in a process for the preparation of crystalline O-isopropylisourea hydrochloride, wherein cyanamide, chloroformamidinium chloride and isopropanol are reacted, an aprotic organic solvent is added thereto before, during and/or and after the reaction and, optionally after cooling the reaction solution, the crystalline reaction product is separated off.

Surprisingly, it has been found that by virtue of this process, the reaction product can be obtained in a very pure and coarse crystalline form which can easily be separated from the reaction solution.

Thus, in the case of the process according to the present invention, cyanamide, chloroformamidinium chloride and isopropanol are brought to reaction. The mol ratio of cyanamide to chloroformamidinium chloride can hereby be varied within relative wide limits but a noticeable excess or insufficiency of chloroformamidinium chloride is preferably avoided. A reaction mixture corresponding to a mol ratio of cyanamide to chloroformamidinium chloride of 1:0.5 to 1:2 is preferably used.

In to an especially preferred embodiment of the process of the present invention, an equimolar or substantially equimolar mixture of cyanamide and chloroformamidinium chloride is used. The ratio of cyanamide to isopropanol can also be varied within wide limits but it is especially advantageous to use 2 to 10 mol and preferably 2.5 to 3.5 mol of isopropanol per mol of cyanamide.

According to an especially preferred embodiment, the chloroformamidinium chloride required for the preparation can be produced, without subsequent isolation, from hydrogen chloride and cyanamide in isopropanol, optionally in the presence of a further solvent, for example, an ether or ester and preferably isopropyl acetate.

It is also possible to produce the reaction mixture of cyanamide and chloroformamidinium chloride in situ by reaction of excess cyanamide and hydrogen chloride in isopropanol, optionally in the presence of a further solvent.

It is important in the present invention that an organic solvent is added to the reaction mixture before, during and/or after the reaction in order thus to dilute the reaction mixture. An aprotic solvent is preferably used an the organic solvent and especially one selected from the group comprising ketones, ethers, esters and acetels and especially preferably in such an amount that 50 to 1000 g and especially 300 to 500 g of organic solvent are used per 1 mol of cyanamide.

Preferred organic solvents are acetone or isopropyl acetate. Naturally, there can also be used further ethers, for example diethyl ether, tetrahydrofurane, as well as esters, for example ethyl acetate, or acetels, for example acetaldehyde dimethyl acetal.

The carrying out of the reaction, which preferably takes place at a temperature of from 0 to 100° C. and especially of from 30 to 60° C., is relatively noncritical, i.e. for example cyanamide and isopropanol can be taken and chloroformamidinium chloride added thereto. Instead thereof, one can also take the isopropanol and add thereto cyanamide and chloroformamidinium chloride successively or simultaneously.

After carrying out the reaction or addition of the organic solvent, especially when having worked at relatively high temperatures, it is preferred to cool the reaction mixture to 10 to 15° C. and then to separate off the thereby resulting crystalline reaction product by known methods, especially by filtration. The crystallisation can be accelerated by seeding with O-isopropylisourea hydrochloride.

In this manner, the preparation of O-isopropylisourea hydrochloride is possible in a technically simple way from the inexpensive starting materials cyanamide and chloroformamidinium chloride, whereby it is not necessary to concentrate the reaction solution and/or subsequently to keep it at low temperatures for a comparatively long period of time.

Furthermore, by means of the process of the present invention, it is possible to obtain an O-isopropylisourea hydrochloride with high purity which has a distinctly higher melting point than the product according to the prior art. The melting point is preferably at least 80° C. especially preferably at least 90° C. and most preferably in the range of from 95 to 100° C.

A further advantage of the process according to the present invention is that neither hydrogen chloride nor isopropyl chloride are liberated as by-products. Furthermore, in the case of the process according to the present invention, the total chlorine in the chloroformamidinium chloride is utilized whereas according to the prior art, half of the chlorine content is converted into isopropyl chloride as an undesired by-product.

Because of these special advantages, the process of the present invention is especially well suited for carrying out on a technical scale.

The following Examples are given for the purpose of illustrating the present invention.

EXAMPLE 1

To a solution of 126.6 g (3.0 mol) of 99.6% crystalline cyanamide (SKW cyanamide F 1000) in 625 g of isopropanol were added at 20° C., while stirring, 345 g (3.0 mol) of chloroformamidinium chloride (SKW Trostberg AG). Subsequently, the reaction mixture was warmed to 30° C. and stirred at this temperature until cyanamide could no longer be detected in the reaction mixture. (The cyanamide detection took place with ammoniacal silver nitrate solution). The reaction time was 130 hours. 1245 g of acetone were then added thereto, followed by stirring for 6 hours at 15° C. The crystalline precipitate obtained was filtered off with suction, washed with 190 g of acetone and dried in a vacuum drying cabinet at 50° C. and 20 mbar pressure. The yield obtained was 518 g (3.74 mol) of O-isopropylisourea hydrochloride with the melting point of 98–99° C. (capillary in a melting block). The literature melting point is 57–61° C. (see DE 19 48 370).

The elementary analysis of the product gave the following results:

C calc. 34.66% found 34.56%
H calc. 8.00% found 7.97%
Cl calc. 25.58% found 25.60%
N calc. 20.21% found 20.34%
urea:<0.10%

EXAMPLE 2

253.5 g (6.0 mol) of 99.6% crystalline cyanamide (SKW cyanamide F 1000) were dissolved in a mixture of 650 g of isopropanol and 1500 g of isopropyl acetate. 218.8 g (6.0 mol) of hydrogen chloride were passed, with stirring and external cooling, into this solution in such a manner that the internal temperature did not increase above 15° C.

Subsequently, the reaction mixture consisting of 126.1 g (3.0 mol) of cyanamide and 345 g (3.0 mol) of chloroformamidinium chloride was heated to 50° C. and stirred at this temperature for 16 hours. Thereafter, the reaction mixture was cooled to 15° C. and further stirred at this temperature for 6 hours. The crystalline residue obtained was filtered off with suction, washed with acetone and dried in a vacuum at 15 mbar pressure. The yield obtained was 682 g (49.2%) of pure O-isopropylisoures hydrochloride; m.p. 98° C.

EXAMPLE 3

160 g of isopropanol were placed in a reaction vessel and heated to 60° C. At this temperature, 42.1 g (1.0 mol) of 99.8% crystalline cyanamide (SKW cyanamide F 1000) and 115 g (1.0 mol) chloroformamidinium chloride were added portionwise in equimolar amounts over the course of 4 hours with good stirring. Thereafter, the reaction mixture was further stirred for 6 hours at 60° C. After the addition of 300 g of acetone, the reaction mixture was cooled to 14° C. and further stirred for 4 hours with water cooling. The crystslline reaction product obtained was filtered off with suction, washed with 80 g of acetone and dried in a vacuum drying cabinet at 50° C. and 15 mbar pressure. The yield obtained was 224 g (1.62 mol) of O-isopropylisourea hydrochloride; m.p. 97–99° C. It will be understood that the specification and examples are illustrative but not limitative of the present invention and that other embodiments within the spirit and scope of the inventions will suggest themselves to those skilled in the art.

I claim:

1. A process for the preparation of crystalline O-isopropylisourea hydrochloride, comprising: (a) reacting cyanamide, chloroformamidinium chloride and isopropanol in a reaction mixture to form a crystalline reaction product; (b) adding an aprotic organic solvent to the reaction mixture before, during and/or after the reaction; and, (c) separating off the crystalline reaction product.

2. The process of claim 1 wherein the reaction solution is cooled prior to step (c).

3. The process of claim 1 wherein the reaction takes place at a temperature of from 0° C. to 100° C.

4. The process of claim 1 wherein the aprotic organic solvent is selected from the group consisting of ketones, ethers, esters, and acetals.

5. The process of claim 1 wherein the mole ratio of cyanamide to chloroformamidinium chloride is from 1:0.5 to 1:2.

6. The process of claim 1 wherein 2 to 10 moles of isopropanol are used per mole of cyanamide.

7. The process of claim 1 wherein 2.5 to 3.5 moles of isopropanol are used per mole of cyanamide.

8. The process of claim 1 wherein the aprotic organic solvent is used in an amount of 50 to 1000 g per mole of cyanamide.

9. The process of claim 1 wherein the organic solvent is used in an amount of 300 to 500 g per mole of cyanamide.

10. The process of claim 1 wherein the aprotic organic solvent is acetone.

11. The process of claim 1 wherein the aprotic organic solvent is isopropyl acetate.

12. The process of claim 1 wherein the chloroformamidinium chloride is produced, without subsequent isolation, from hydrogen chloride and cyanamide in isopropanol, optionally in the presence of a further solvent.

13. The process of claim 1 wherein a mixture of cyanamide and chloroformamidinium chloride is prepared in situ by the reaction of cyanamide and hydrogen chloride in isopropanol, optionally in the presence of a further solvent.

14. The process of claim 1 wherein the reaction is carried out at a temperature of 30° to 60° C.

15. The process of claim 1 wherein, after the reaction, the reaction mixture is cooled to a temperature of from 10 to 1° C.

16. The process of claim 15 wherein the reaction mixture is seeded by the addition of crystalline O-isopropylisourea hydrochloride.

* * * * *

UNITED STATES PATENT AND TRADEMARK OFFICE
CERTIFICATE OF CORRECTION

PATENT NO. : 5,705,666

DATED : January 6, 1998

INVENTOR(S) : Stefan WEISS

It is certified that error appears in the above-identified patent and that said Letters Patent is hereby corrected as shown below:

In column 2, line 57, change "acetels" to --acetals--.

In column 2, line 64, change "acetels" to --acetals--.

In column 3, line 2, change "end" to --and--.

In column 3, line 25, after "80° C." add -- , --.

In column 3, line 65, change "25,58%" to --25.58%--.

In column 4, line 4, change "end" to --and--.

In column 4, line 16, change "O-isopropylisoures" to --O-isopropylisourea--.

In column 4, line 27, change "cystslline" to --crystalline--.

UNITED STATES PATENT AND TRADEMARK OFFICE
CERTIFICATE OF CORRECTION

PATENT NO. : 5,705,666
DATED : January 6, 1998
INVENTOR(S) : Stefan WEISS

It is certified that error appears in the above-identified patent and that said Letters Patent is hereby corrected as shown below:

In column 4, lines 32-36, the sentence "It will be . . . in the art." should be a separate paragraph.

In Claim 15, column 6, line 2, change "1° " to --15°--.

Signed and Sealed this

Third Day of August, 1999

Attest:

Q. TODD DICKINSON

Attesting Officer

Acting Commissioner of Patents and Trademarks